United States Patent
Kim et al.

(10) Patent No.: US 11,241,219 B2
(45) Date of Patent: Feb. 8, 2022

(54) ULTRASOUND SYSTEM AND METHOD FOR GENERATING ELASTIC IMAGE

(71) Applicant: Siemens Medical Solutions USA, Inc., Malvern, PA (US)

(72) Inventors: Jihwan Kim, Incheon (KR); Hanju Moon, Seongnam-si (KR); Jangkun Kim, Yongin-si (KR)

(73) Assignee: Siemens Medical Solutions USA, Inc., Malvern, PA (US)

( * ) Notice: Subject to any disclaimer, the term of this patent is extended or adjusted under 35 U.S.C. 154(b) by 520 days.

(21) Appl. No.: 15/253,697

(22) Filed: Aug. 31, 2016

(65) Prior Publication Data

US 2017/0065256 A1   Mar. 9, 2017

(30) Foreign Application Priority Data

Sep. 3, 2015   (KR) .................. 10-2015-0124775

(51) Int. Cl.
*A61B 8/08*   (2006.01)
*A61B 8/00*   (2006.01)

(52) U.S. Cl.
CPC ............ *A61B 8/5207* (2013.01); *A61B 8/485* (2013.01); *A61B 8/488* (2013.01); *A61B 8/54* (2013.01); *A61B 8/463* (2013.01); *A61B 8/5223* (2013.01)

(58) Field of Classification Search
CPC ......... A61B 8/5207; A61B 8/54; A61B 8/488; A61B 8/485; A61B 8/5223; A61B 8/46
See application file for complete search history.

(56) References Cited

U.S. PATENT DOCUMENTS

| | | | | |
|---|---|---|---|---|
| 5,313,947 A | * | 5/1994 | Micco | A61B 8/06 600/455 |
| 5,749,364 A | * | 5/1998 | Sliwa, Jr. | A61B 8/08 600/438 |

(Continued)

FOREIGN PATENT DOCUMENTS

| | | |
|---|---|---|
| CN | 1798524 A | 7/2006 |
| CN | 101933820 A | 1/2011 |

(Continued)

OTHER PUBLICATIONS

EP Search Report dated Aug. 27, 2015 from EP application No. EP 15 16 1294, 6 pages total.

(Continued)

*Primary Examiner* — Rochelle D Turchen

(57) ABSTRACT

An ultrasound system and method for generating an elastic image are disclosed. The ultrasound system includes an ultrasound probe and a processor. The ultrasound probe is configured to transmit ultrasound signals into a target object and receive ultrasound echo signals from the target object while the ultrasound probe applies a variable compression force on the target object. The processor is configured to set a Doppler gate at a predetermined location in an image of the target object, generate a plurality of frames of B-mode ultrasound data while the variable compression force is applied on the target object based on the ultrasound echo signals, generate a plurality of frames of Doppler-mode ultrasound data based on the Doppler gate while the variable compression force is applied on the target object based on the ultrasound echo signals, determine a period for a cycle of the variable compression force based on the Doppler-mode ultrasound data, select two frames of the B-mode ultrasound data based on the period, and generate an elastic (Continued)

image of the target object based on the selected frames of the B-mode ultrasound data.

16 Claims, 7 Drawing Sheets

(56) References Cited

U.S. PATENT DOCUMENTS

| | | | |
|---|---|---|---|
| 5,797,849 A | 8/1998 | Vesely et al. | |
| 5,873,830 A | 2/1999 | Hossack et al. | |
| 6,293,914 B1* | 9/2001 | Sumanaweera | A61B 8/06 600/443 |
| 6,450,959 B1 | 9/2002 | Mo et al. | |
| 7,678,051 B2 | 3/2010 | Fan et al. | |
| 10,143,439 B2 | 12/2018 | Osumi et al. | |
| 2004/0000627 A1 | 1/2004 | Schuster | |
| 2005/0187470 A1* | 8/2005 | Kubota | A61B 8/08 600/437 |
| 2007/0049824 A1 | 3/2007 | Konofagou | |
| 2008/0021319 A1 | 1/2008 | Hamilton | |
| 2008/0188743 A1 | 8/2008 | Waki et al. | |
| 2008/0269606 A1* | 10/2008 | Matsumura | A61B 5/0048 600/438 |
| 2009/0003665 A1 | 1/2009 | Berg et al. | |
| 2010/0041994 A1* | 2/2010 | Abe | A61B 8/429 600/443 |
| 2010/0138191 A1 | 6/2010 | Hamilton | |
| 2011/0112403 A1* | 5/2011 | Machtey | A61B 8/02 600/443 |
| 2011/0306883 A1 | 6/2011 | Park | |
| 2012/0065507 A1 | 3/2012 | Brunke | |
| 2012/0092527 A1 | 4/2012 | Lavin et al. | |
| 2012/0108965 A1* | 5/2012 | Lazebnik | A61B 8/4254 600/438 |
| 2012/0296214 A1* | 11/2012 | Urabe | A61B 8/0858 600/444 |
| 2013/0123630 A1 | 5/2013 | Freiburger et al. | |
| 2013/0218012 A1 | 8/2013 | Specht | |
| 2014/0303499 A1* | 10/2014 | Toma | A61B 8/06 600/454 |
| 2015/0042657 A1 | 2/2015 | Smith-Casem et al. | |
| 2015/0126867 A1 | 5/2015 | Osumi | |
| 2015/0209013 A1 | 7/2015 | Tsymbalenko | |
| 2015/0272547 A1 | 10/2015 | Freiburger et al. | |

FOREIGN PATENT DOCUMENTS

| | | | |
|---|---|---|---|
| CN | 104507395 A | 4/2015 | |
| CN | 104739442 A | 7/2015 | |
| CN | 105395218 A | 3/2016 | |
| EP | 2387948 A1 | 11/2011 | |
| JP | 2003250803 A | 9/2003 | |
| JP | 2007236606 A | 9/2007 | |
| JP | 20120610075 A | 3/2012 | |
| KR | 20150047447 A | 5/2015 | |
| WO | 20040089222 A1 | 10/2004 | |
| WO | WO-2011096556 A1 * | 8/2011 | A61B 8/06 |

OTHER PUBLICATIONS

RR Bouchard, et al., "Image Quality, Tissue Heating, and Frame Rate Trade-offs in Acoustic Radiation Force Impulse Imaging," 2009, IEEE Transactions on Ultrasonics, Ferroelectrics, and Frequency Control, vol. 55, No. 1, pp. 63-76.

* cited by examiner

ULTRASOUND SYSTEM AND METHOD FOR GENERATING ELASTIC IMAGE

CROSS-REFERENCE TO RELATED APPLICATION

This application claims the benefit of Korean Patent Application No. 2015-0124775, filed Sep. 3, 2015, in the Korean Intellectual Property Office, the disclosure of which is incorporated herein in its entirety by reference.

TECHNICAL FIELD

The present disclosure relates to an ultrasound system, and more particularly, to an ultrasound system and method for generating an elastic image.

BACKGROUND ART

Ultrasound systems have been widely used in the medical field to obtain information of interest in a target object. Using high-frequency sound waves, ultrasound systems can provide high-resolution images of the target object in real time without requiring an invasive surgical operation on the target object. Due to the non-invasive nature as well as quality of images, ultrasound systems have become an important tool for diagnosing and treating various medical conditions.

Conventional ultrasound systems typically provide a brightness mode image ("B-mode image") in which reflection coefficients of ultrasound signals (i.e., ultrasound echo signals) reflected from the interested objects in the target object are shown as a two-dimensional image. In such B-mode image, the reflection coefficients of the ultrasound signals on a display are displayed as brightness of pixels. However, since reflection coefficients of anomalous tissues such as a tumor, a cancerous tumor, a diseased tissue, etc. are not different from those of normal tissues, it may be difficult to observe the anomalous tissues with B-mode imaging.

Some ultrasound systems may employ an elastic imaging technique that visualizes the mechanical characteristics of anomalous tissues, which may not be observed in a B-mode image. The elastic imaging technique is often effective in diagnosing anomalous tissue since the elasticity of such tissue is generally different from normal tissue. For example, anomalous tissues such as a tumor, a cancerous tissue, etc. are typically harder than normal tissue. Accordingly, such anomalous tissue is deformed less than normal tissue when a same compression force is applied thereto. As such, the elastic imaging technique uses the phenomenon that hard tissues are less deformed than soft tissues when the same compression forces are applied thereto.

In such conventional elastic imaging technique, displacements between adjacent frames are generally calculated by using ultrasound data acquired during a plurality of time intervals. The period of movement of the ultrasound probe that applies compression force to the target object is then determined by using the calculated displacements. However, such conventional elastic imaging technique typically requires a substantial amount of computation resources for calculating the displacements between adjacent frames. Further, it may be difficult to accurately track movement of a quickly moving ultrasound probe.

The present invention provides an ultrasound system and method for determining a period of movement of an ultrasound probe based on ultrasound data in a Doppler gate that is set at a predetermined location in an image of a target object, and generating an elastic image based on the determined period.

TECHNICAL SOLUTION

In one embodiment, an ultrasound system includes an ultrasound probe, a processor, and a display unit. The ultrasound probe is configured to transmit ultrasound signals to a target object and receive ultrasound echo signals from the target object while a variable compression force is applied on the target object. The processor is configured to set a Doppler gate at a predetermined location in an image of the target object, generate a plurality of frames of B-mode ultrasound data while the variable compression force is applied on the target object based on the ultrasound echo signals, generate a plurality of frames of Doppler-mode ultrasound data based on the Doppler gate while the variable compression force is applied on the target object based on the ultrasound echo signals, determine a period for a cycle of the variable compression force based on the Doppler-mode ultrasound data, select two frames of the B-mode ultrasound data based on the period, and generate an elastic image of the target object based on the selected frames of the B-mode ultrasound data. The display unit is configured to display the elastic image.

In another embodiment, a method for generating an elastic image of a target object in an ultrasound system includes setting a Doppler gate at a predetermined location in an image of the target object, acquiring a plurality of frames of B-mode ultrasound data from the target object while a variable compression force is applied on the target object by an ultrasound probe, acquiring a plurality of frames of Doppler-mode ultrasound data from the target object based on the Doppler gate while the variable compression force is applied on the target object by the ultrasound probe, determining a period for a cycle of the variable compression force based on the Doppler-mode ultrasound data, selecting two frames of the B-mode ultrasound data based on the period, and generating the elastic image of the target object based on the selected frames of the B-mode ultrasound data.

According to the present disclosure, two frames of ultrasound data may be selected based on a period of movement of an ultrasound probe. The selected frames of ultrasound data may then be used to generate an elastic image. By using the selected frames, the amount of computing displacements for generating the elastic image can be substantially reduced.

Further, since an elastic image can be generated by using the selected frames of ultrasound data based on the period of movement of the ultrasound probe, the elastic image may be generated in an efficient manner.

Furthermore, a movement of the ultrasound probe may be traced even when the ultrasound probe is quickly moving. Accordingly, the elastic image can be generated based on the traced movement of the ultrasound probe.

Hereinafter, embodiments of the present disclosure will be described with reference to the accompanying drawings. The term "section" used in these embodiments means a software component or hardware component, such as a field-programmable gate array (FPGA) and an application specific integrated circuit (ASIC). However, a "section" is not limited to software and hardware, and may be configured to be in an addressable storage medium or may be configured to run on one or more processors. For example, a "section" may include components, such as software components, object-oriented software components, class components, and task components, as well as processors, functions, attributes, procedures, subroutines, segments of program codes, drivers, firmware, micro-codes, circuits, data, databases, data structures, tables, arrays, and variables. Functions provided in components and "sections" may be combined into a smaller number of components and "sections" or further subdivided into additional components and "sections."

Figure 1:
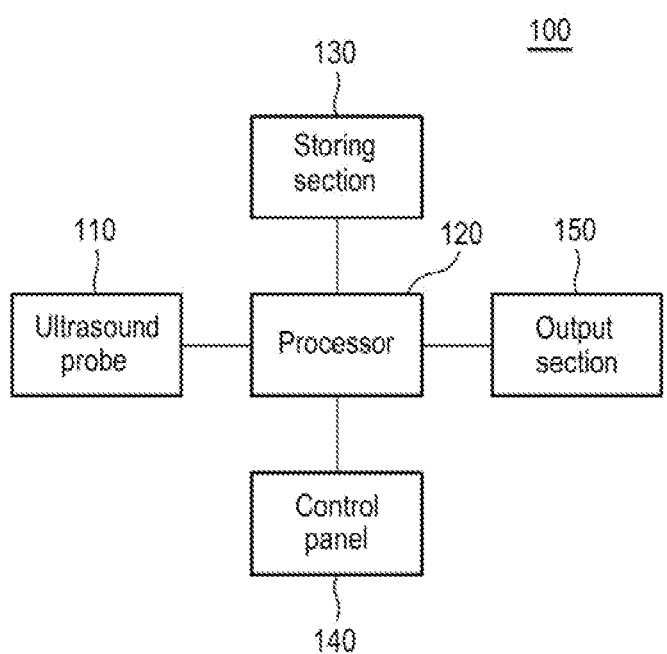
FIG. 1 is a block diagram schematically showing a configuration of an ultrasound system according to an embodiment of the present disclosure.

FIG. 1 is a block diagram schematically showing a configuration of an ultrasound system 100 according to an embodiment of the present disclosure. The ultrasound system 100 includes an ultrasound probe 110, a processor 120, a storing section 130, a control panel 140, and an output section 150. In the illustrated embodiment, the processor 120 may be configured to control the ultrasound probe 110, the storing section 130, the control panel 140, and the output section 150.

In the ultrasound system 100, the storing section 130 stores ultrasound data (e.g. B-mode ultrasound data, Doppler-mode ultrasound data or the like), which are obtained by the processor 120, on a frame by frame in chronological order. Further, the storing section 130 stores instructions for operating the ultrasound system 100.

The control panel 140 receives input information from a user, and transmits the received input information to the processor 120. The control panel 140 may include an input section (not shown), which allows the user to interface with and/or operate the ultrasound system 100. The input section may include any suitable input devices, such as, a trackball, a keyboard, buttons, etc. for selecting diagnosis modes, controlling diagnosis operations, inputting suitable commands for diagnosis, controlling signals, controlling output, etc.

In response to the input information received via the control panel 140, the processor 120 may control the ultrasound probe 110 in transmitting ultrasound signals to a target object and receiving ultrasound signals (i.e., ultrasound echo signals) from the target object. Further, the processor 120 may form one or more ultrasound image of the target object based on the received ultrasound signals for output on the output section 150. Further, the processor 120 may set a Doppler gate at a predetermined location in an image of the target object.

The output section 150 displays ultrasound images (i.e., a B-mode image and an elastic image) that are formed by the processor 120. Further, the output section 150 displays the guidelines, which are formed by the processor 120, as a graph. Further, the output section 150 outputs the guide sound that is formed by the processor 120. The output section 150 comprises a display unit (not shown), a speaker (not shown), etc.

The ultrasound probe 110 includes an ultrasound transducer (not shown) configured to convert electrical signals into ultrasound signals and vice versa. The ultrasound probe 110 transmits ultrasound signals into a target object (not shown) and receives ultrasound signals (i.e., ultrasound echo signals) reflected from the target object. The target object may include an interested object (e.g., a lesion, a tissue, an organ, etc.) (see IO in FIG. 3). Further, the ultrasound probe 110 may apply a force, which may be provided externally, on the target object. In this case, the ultrasound probe 110 may apply a variable compression force on the target object during a period for a cycle of the variable compression force. For example, the variable compression force may be applied during a first time period in which the compression force increases and a second time period in which the compression force decreases. In this manner, the variable compression force may be applied on the target object such that the compression force, which may include a minimum compression force (e.g., no compression force) and a maximum compression force, varies over time.

In some embodiments, the ultrasound probe 110 may apply a variable compression force on the target object while transmitting ultrasound signals into the target object and receiving ultrasound echo signals reflected from the target object. The received ultrasound echo signals are converted into reception signals (hereinafter, referred to as "first reception signals") corresponding to one or more frames (e.g., B-mode image frames), each of which may include a plurality of scanlines. For example, the ultrasound probe 110 transmits ultrasound signals into the target object and receives ultrasound echo signals reflected from the target object during the first time period in which an increasing compression force is applied on the target object and during a second time period in which a decreasing compression force is applied on the target object. In this case, the durations of the first time period and the second time period may be the same or different from each other. The received ultrasound echo signals may be converted by the ultrasound probe 110 into the first reception signals, from which one or more frames of ultrasound data may be generated by the processor 120.

While a variable compression force is being applied on the target object, the ultrasound probe 110 may transmit ultrasound signals into the target object based on the Doppler gate, which is set at a predetermined position in an ultrasound image (e.g., a B-mode image etc.) of the target object, and receive ultrasound echo signals reflected from the target object. The received ultrasound echo signals may be converted by the ultrasound probe 110 into reception signals corresponding to the Doppler gate (hereinafter, referred to as "second reception signals"). For example, the ultrasound probe 110 may transmit ultrasound signals into the target object and receive ultrasound echo signals reflected from the target object based on the Doppler gate during the first time period in which the increasing compression force is applied on the target object and during the second time period in which the decreasing compression force is applied on the target object.

The received ultrasound echo signals may be converted by the ultrasound probe 110 into the second reception signals, from which one or more frames of Doppler-mode ultrasound data may be generated by the processor 120. The processor 120 determines a period for a cycle of the variable compression force based on the second reception signals, and selects two frames of the ultrasound images (e.g., B-mode images) based on the period for the cycle of the variable compression force. The processor 120 may then generate an elastic image of the target object (e.g., the interested object) based on the selected frames and output the elastic image on the output section 150.

Figure 2:
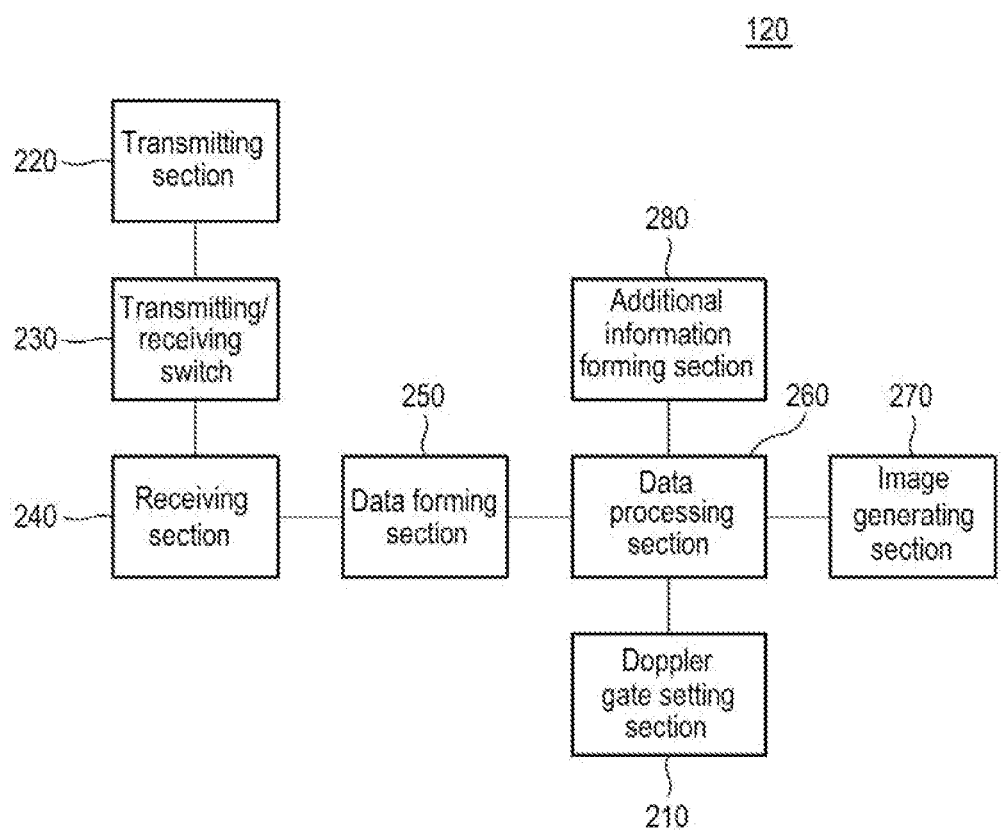
FIG. 2 is a block diagram schematically showing a configuration of a processor according to an embodiment of the present disclosure.

FIG. 2 is a block diagram schematically showing a configuration of the processor 120 according to an embodiment of the present disclosure. The processor 120 includes a Doppler gate setting section 210, which is configured to set the Doppler gate (see "DG" in FIG. 3.) at a predetermined location in an image (i.e., an image displayed on the output section 150) of the target object. In one embodiment, the Doppler gate DG may be set to obtain ultrasound data that can be used to determine a period for a cycle of variable compression force that is applied on the target object. For example, the Doppler gate DG may be set to obtain ultrasound data that can be used to determine a period for movement of the ultrasound probe 110 over the first and second time periods.

Figure 3:
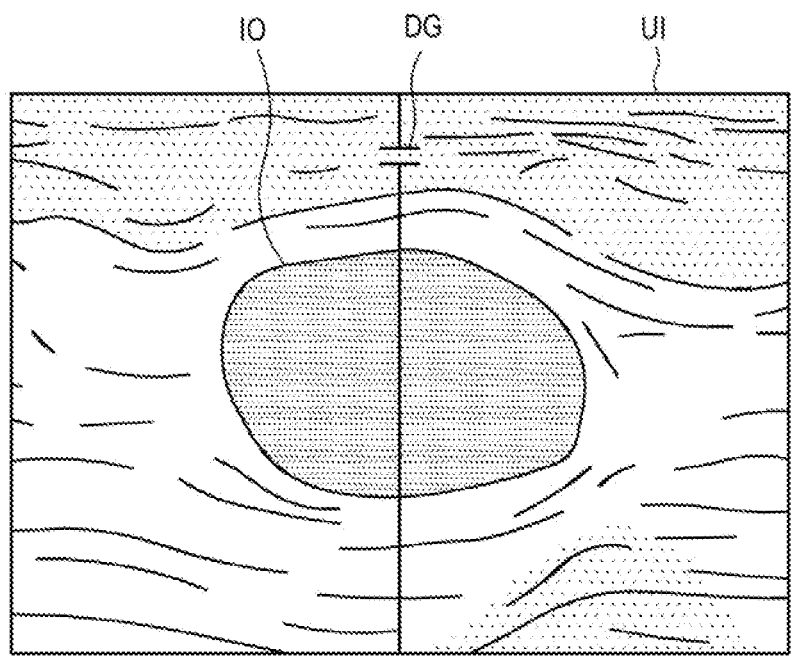
FIG. 3 is an illustrative view showing a Doppler gate according to an embodiment of the present disclosure.

In one embodiment, the Doppler gate setting section 210 may set the Doppler gate DG at a predetermined location in an ultrasound image (e.g., B-mode image) UI of the target object based on a center portion of the ultrasound transducer of the ultrasound probe 110, as shown FIG. 3. The predetermined location may be within 1 cm from the surface of the target object. Generally, the target object comprises one or more interested objects, which reside at a depth of 1 cm or more from the surface of the target object, and soft tissues (e.g., skin, fibrous tissue, fat, etc.), which reside at a depth within 1 cm from the surface of the target object. Accordingly, the ultrasound data acquired from portions within 1 cm from the surface of the target object, which contacts the ultrasound probe 110, may reflect movement of the ultrasound probe 110.

Referring back to FIG. 2, the processor 120 further includes a transmitting section 220. The transmitting section 220 forms transmission signals for acquiring ultrasound data corresponding to a plurality of frames (e.g., B-mode images or the like).

In one embodiment, the transmitting section 220 forms transmission signals (hereinafter, referred to as "first transmission signals") for acquiring each of the plurality of frames of B-mode ultrasound data during the first and second time periods. The first transmission signals are provided to the ultrasound probe 110, which transforms the first transmission signals into ultrasound signals and transmits the transformed ultrasound signals to the target object. The ultrasound probe 110 receives ultrasound echo signals reflected from the target object to form the first reception signals.

Further, the transmitting section 220 forms transmission signals (hereinafter, referred to as "second transmission signals") for acquiring a plurality of frames of Doppler-mode ultrasound data corresponding to the Doppler gate DG during the first and second time periods. The second transmission signals are provided to the ultrasound probe 110, which transforms the signals into ultrasound signals and transmits the ultrasound signals to the target object. The ultrasound probe 110 receives ultrasound echo signals reflected from the target object and forms the second reception signals.

According to one embodiment, the transmitting section 220 may generate first and second transmission signals based on a pulse repetition frequency (or a pulse repetition period) associated with each of the B-mode image and the Doppler gate.

Figure 4:
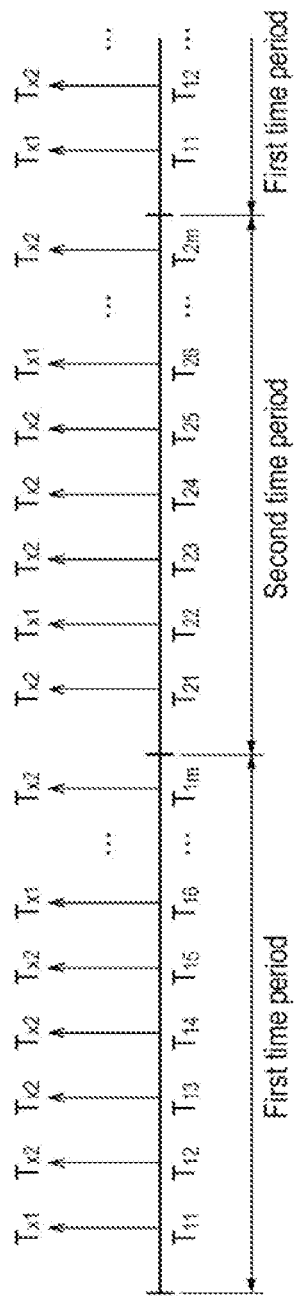
FIG. 4 is an illustrative view showing transmitting and receiving of ultrasound signals according to an embodiment of the present disclosure.

For example, the transmitting section 220 may generate the first transmission signals at a time $T_{11}$ based on the pulse repetition frequency associated with the B-mode image, as shown in FIG. 4, and provide the first transmission signals to the ultrasound probe 110. Upon receiving the first transmission signals, the ultrasound probe 110 transforms the signals into the ultrasound signals, transmits the ultrasound signals to the target object (as shown as $T_{x1}$ in FIG. 4), and forms the first reception signals upon receiving ultrasound echo signals reflected from the target object.

Further, the transmitting section 220 may generate second transmission signals at each of the times $T_{12}$ to $T_{15}$ based on the pulse repetition frequency associated with the Doppler gate DG, and provide the second transmission signals to the ultrasound probe 110. The pulse repetition frequency of the Doppler gate DG may be less than or equal to 100 Hz. Upon receiving the second transmission signals, the ultrasound probe 110 transforms the signals into the ultrasound signals, transmits the ultrasound signals to the target object (shown as $T_{x2}$ in FIG. 4), and forms the second reception signals upon receiving the ultrasound echo signals reflected from the target object.

Subsequently, the transmitting section 220 may generate first transmission signals at a time $T_{16}$, and provide the first transmission signals to the ultrasound probe 110. Upon receiving the first transmission signals, the ultrasound probe 110 transforms the first transmission signals into ultrasound signals, transmits the transformed ultrasound signals to the target object (shown as $T_{x1}$ in FIG. 4), and forms first reception signals upon receiving ultrasound echo signals reflected from the target object.

As explained above, the transmitting section 220 generates the transmission signals (i.e., the first and/or second transmission signals) during the first and second time periods, based on the pulse repetition frequency (or a pulse repetition period) associated with each of the B-mode image and the Doppler gate, and provides the formed transmission signals to the ultrasound probe 110.

Referring back to FIG. 2, the processor 120 further includes a transmitting/receiving switch 230 and a receiving section 240. The transmitting/receiving switch 230 serves as a duplexer to switch between the transmitting section 220 and the receiving section 240, so that the transmitting section 220 and the receiving section 240 are not affected by transmission of signals from one another. For example, the transmitting/receiving switch 230 operates to properly switch or electrically connect the transmitting section 220 or the receiving section 240 to the ultrasound probe 110 (i.e., the ultrasound transducer) when the ultrasound probe 110 alternatively performs transmitting and receiving.

In the processor 120, the receiving section 240 may be configured to amplify reception signals received from the ultrasound probe 110 via the transmitting/receiving switch 230, and transform the amplified reception signals into digital signals. The receiving section 240 may include a time gain compensation (TGC) unit (not shown) for compensating attenuation that typically occurs when ultrasound signals pass through the target object, and an analog to digital conversion unit (not shown) for transforming analog signals into digital signals, etc.

In one embodiment, the receiving section 240 amplifies the first reception signals received from the ultrasound probe 110, and transforms the amplified first reception signals into digital signals (hereinafter, referred to as "first digital signals"). Further, the receiving section 240 amplifies the second reception signals received from the ultrasound probe 110, and transforms the amplified second reception signals into digital signals (hereinafter, referred to as "second digital signals").

The processor 120 further includes a data forming section 250. The data forming section 250 generates ultrasound data based on the digital signals provided form the receiving section 240. The ultrasound data comprises radio frequency (RF) data or in-phase/quadrature (IQ) data, but are not limited thereto.

In one embodiment, the data forming section 250 generates ultrasound data (hereinafter, referred to as "B-mode ultrasound data") for each of the plurality of frames based on the first digital signals provided from the receiving section 240. In this process, a plurality of B-mode ultrasound data corresponding to the plurality of frames may be generated sequentially. Further, the data forming section 250 generates ultrasound data for each of the plurality of the frames corresponding to the Doppler gate DG (hereinafter, referred to as "Doppler-mode ultrasound data") based on the second digital signals provided from the receiving section 240. In this process, a plurality of Doppler-mode ultrasound data corresponding to the plurality of frames may be sequentially generated.

The processor 120 further includes a data processing section 260. The data processing section 260 performs data processing on the ultrasound data (i.e., the B-mode ultrasound data and the Doppler-mode ultrasound data), which are provided from the data forming section 250.

In one embodiment, the data processing section 260 determines the period for the cycle of the variable compression force applied on the target object based on the Doppler-mode ultrasound data provided from the data forming section 250, and selects two frames of the B-mode ultrasound data based on the determined period. For example, the data processing section 260 may include a filtering section (not shown), a center frequency determining section (not shown), a period determining section (not shown), and a frame selecting section (not shown).

The filtering section adds Doppler-mode ultrasound data corresponding to a plurality of sampling points (not shown) within the Doppler gate DG and filters the added data to form filtered data. In one example, the filtering section comprises a low pass filter and a cutoff frequency of the low pass filer may be 20 Hz. Generally, since the movement of the ultrasound probe 110 is 20 Hz or less, the cutoff frequency of the low pass filter may be set to 20 Hz or less.

The center frequency determining section determines a center frequency based on the filtered data. In one embodiment, the center frequency determining section performs Fourier transformation on the filtered data, determines a bandwidth on the Fourier transformed data (i.e., the data in the frequency domain), and calculates a mean frequency of the determined bandwidth as the center frequency.

The period determining section determines a period of movement of the ultrasound probe 110 (i.e., a period for the cycle of the variable compression force that is applied on the target object) based on the center frequency. According to one embodiment, the period determining section may determine the period according to the following equation:

$$T = \frac{1}{f_c} \qquad \text{Equation (1)}$$

where T represents the period of movement of the ultrasound probe 110 and $f_c$ represents the center frequency.

The frame selecting section selects two frames (i.e., two frames of the B-mode ultrasound data) for generating an elastic image based on the determined period. In one embodiment, the frame selecting section may select a first frame from the plurality of frames of B-mode ultrasound data, and select a second frame, which precedes the first frame, from the plurality of frames of B-mode ultrasound data based on the period of movement of the ultrasound probe 110. In this case, the first frame may be a current frame and the second frame may be a frame that precedes the first frame by a specified number of frames, which may be calculated according to the following equation:

$$F = \frac{T \times F_r}{2} \qquad \text{Equation (2)}$$

where F represents the specified number of frames, T represents the period of movement of the ultrasound probe 110, and $F_r$ represents a frame rate of the plurality of frames of B-mode ultrasound data (i.e., B-mode image).

According to the above equation (2), when the period T of movement of the ultrasound probe 110 is 0.4 and the frame rate $F_r$ of the B-mode image is 20, the frame selecting section calculates the specified number of frames to be 4.

Figure 5:
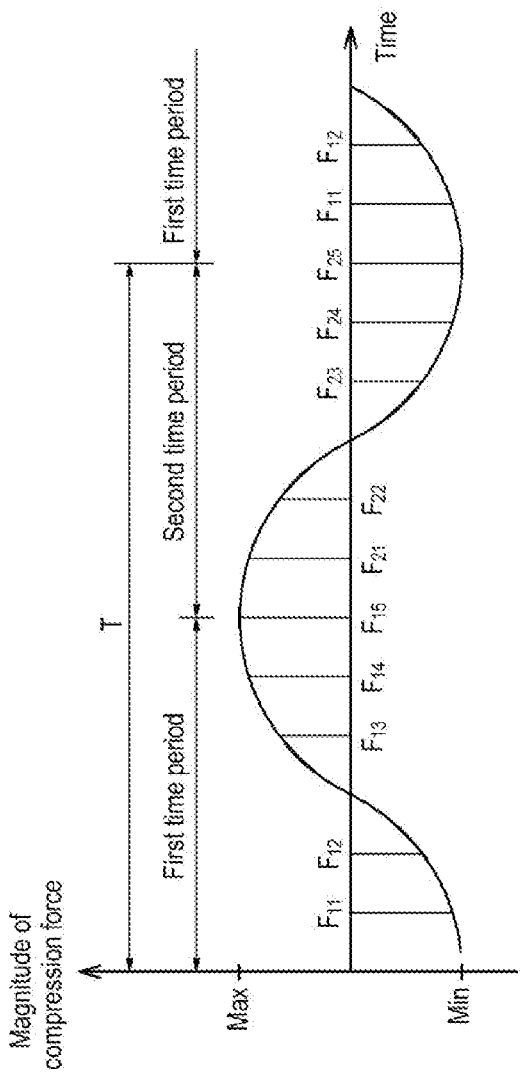
FIG. 5 is an illustrative view showing a plurality of frames according to an embodiment of the present disclosure.

In the embodiment shown in FIG. 5, the frame selecting section may select one frame $F_{25}$ as the first frame. Further, the frame selecting section may select a frame $F_{15}$, which skips the previous four frames $F_{24}, F_{23}, F_{22}, F_{21}$ based on the first frame $F_{25}$, as the second frame, based on the specified number of frames (e.g., F=4), which is calculated by the above equation (2).

Referring back to FIG. 2, the processor 120 further includes an image generating section 270. The image generating section 270 generates an elastic image based on the B-mode ultrasound data of the two selected frames. Additionally, the image generating section 270 generates an image (e.g., B-mode image) of the target object based on the B-mode ultrasound data that are provided from the data forming section 250.

In the embodiment illustrated in FIG. 5, the image generating section 270 may generate an elastic image based on the B-mode ultrasound data of the first frame $F_{25}$ and the B-mode ultrasound data of the second frame $F_{15}$. Since the elastic image may be generated by various known methods, a detailed explanation thereon is omitted.

Referring back to FIG. 2, the processor 120 further includes an additional information forming section 280, which forms additional information based on the center frequency calculated by the data processing section 260.

Figure 6:
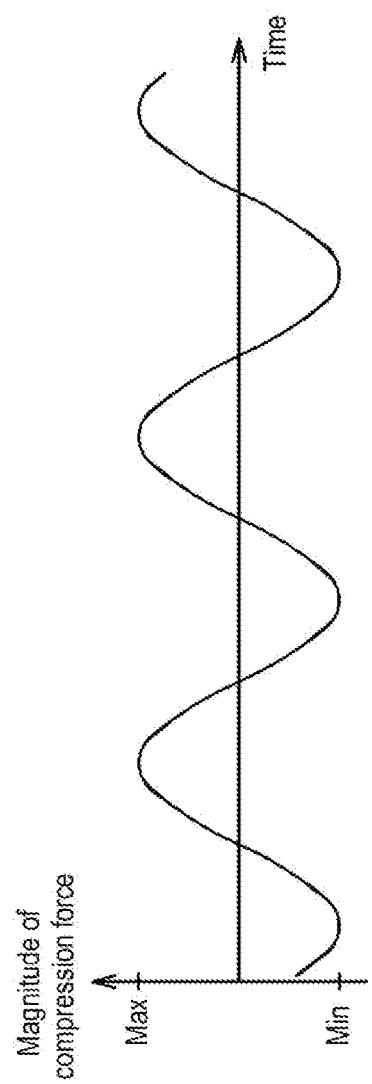
FIG. 6 is an illustrative view showing additional information according to an embodiment of the present disclosure.

In one embodiment, the additional information forming section 280 may further include a guideline forming section (not shown) that is configured to form a guideline for guiding the movement of the ultrasound probe 110 as the additional information, as shown in FIG. 6, based on the center frequency calculated from the data processing section 260. In FIG. 6, the horizontal axis represents time, while the vertical axis represents a magnitude of a variable compression force.

In some embodiments, the additional information forming section 280 determines a time (hereinafter, "maximum applied time") when a maximum compression force is applied on the target object, based on the center frequency calculated by the data processing section 260. The additional information forming section 280 may include a guide sound generating section (not shown) configured to form guide sound as additional information to guide the determined maximum applied time. For example, the guide sound generating section may be set to output a specific sound (e.g., beep sound) at a location that represents the maximum compression force in FIG. 6.

Figure 7:
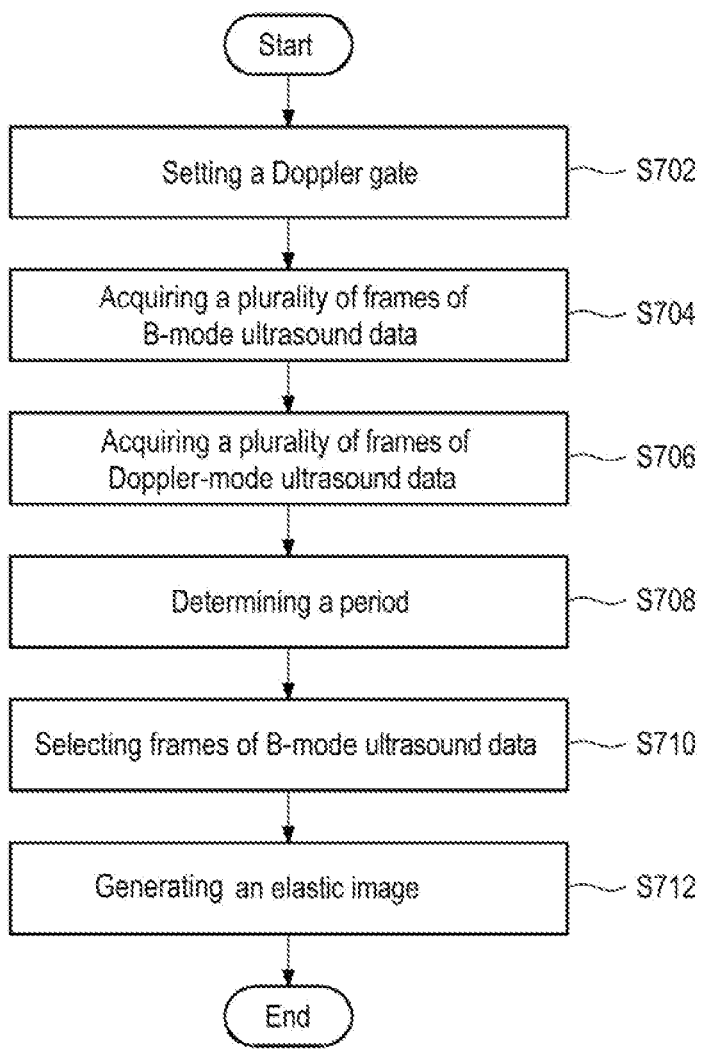
FIG. 7 is a flowchart illustrating a procedure of generating an elastic image according to an embodiment of the present disclosure.

FIG. 7 is a flowchart illustrating a method of generating an elastic image according to one embodiment of the present disclosure. The processor 120 sets the Doppler gate at the predetermined location in the image of the target object, as shown in FIG. 3 (S702).

The processor 120 generates a plurality of frames of B-mode ultrasound data from the target object during the first time period and the second time period (S704). The processor 120 also generates a plurality of frames of Doppler-mode ultrasound data from the target object based on the Doppler gate DG during the first time period and the second time period (S706).

The processor 120 then determines a period for the cycle of the variable compression force based on the Doppler-mode ultrasound data (S708). That is, the processor 120 determines the period of movement of the ultrasound probe 110, which applies the variable compression force on the target object target object during the first and second time periods, based on the Doppler-mode ultrasound data. As described above, the period may be calculated according to the above equation (1).

Upon determining the period for the cycle of the variable compression force, the processor 120 selects B-mode ultrasound data of two frames for generating the elastic image based on the determined period (S710). In one embodiment, the processor 120 may calculate a specified number of frames based on the above equation (2); select a first frame from the plurality of frames of B-mode ultrasound data; and select a second frame that precedes the first frame among the plurality of frames of B-mode ultrasound data by the specified number of frames.

Based on the selected first frame of the B-mode ultrasound data and second frame of the B-mode ultrasound data, the processor 120 generates the elastic image (S712) for display via the output section 150.

While certain embodiments have been described, these embodiments have been presented by way of example only, and are not intended to limit the scope of the disclosures. Indeed, the novel methods and apparatuses described herein may be embodied in a variety of other forms; furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures.

What is claimed is:

1. A method for generating an elastic image of a target object in an ultrasound system, comprising:
    setting a Doppler gate at a predetermined location in an image of the target object;
    acquiring a plurality of frames of B-mode ultrasound data from the target object while an ultrasound probe movement applies a variable compression force on the target object;
    acquiring a plurality of frames of Doppler-mode ultrasound data from the target object based on the Doppler gate while the ultrasound probe movement applies the variable compression force on the target object;
    determining a period for a cycle of the ultrasound probe movement based on the Doppler-mode ultrasound data, wherein determining the period comprises:
        filtering the Doppler-mode ultrasound data;
        calculating a center frequency of the filtered Doppler-mode ultrasound data; and
        determining the period for the cycle of the ultrasound probe movement based on the center frequency;
    selecting two frames of the B-mode ultrasound data based on the period for the cycle of the ultrasound probe movement; and
    generating the elastic image of the target object based on the selected frames of the B-mode ultrasound data.

2. The method of claim 1, wherein filtering the Doppler-mode ultrasound data comprises filtering the Doppler-mode ultrasound data by using a low pass filter.

3. The method of claim 1, wherein the plurality of frames of B-mode ultrasound data are acquired sequentially, and wherein selecting the two frames of the B-mode ultrasound data comprises:
    selecting a first frame from the plurality of frames of B-mode ultrasound data; and
    selecting a second frame from the frames of B-mode ultrasound data preceding the first frame based on the period.

4. The method of claim 3, wherein the second frame precedes the first frame by a specified number of frames, and wherein selecting the second frame from the frames of B-mode ultrasound data comprises calculating the specified number of frames according to the following equation:

$$F = \frac{T \times F_r}{2}$$

wherein F represents the specified number of frames, T represents the period, and $F_r$ represents a frame rate for the frames of the B-mode ultrasound data.

5. The method of claim 1, wherein the predetermined location of the Doppler gate is within 1 cm from a surface of the target object when the surface is in contact with the ultrasound probe.

6. The method of claim 1, wherein a pulse repetition frequency for each of the plurality of the frames of the Doppler-mode ultrasound data is less than or equal to 100 Hz.

7. The method of claim 1, further comprising:
    generating a guideline configured to guide movement of the ultrasound probe based on the period; and
    displaying the guideline as a graph.

8. The method of claim 1, further comprising:
    generating guide sound configured to guide the ultrasound probe movement based on the period; and
    outputting the guide sound.

9. An ultrasound system, comprising:
    an ultrasound probe configured to transmit ultrasound signals into a target object and receive ultrasound echo signals from the target object while applying a variable compression force on the target object;
    a processor configured to set a Doppler gate at a predetermined location in an image of the target object, the predetermined location of the Doppler gate being within 1 cm from a surface of the target object when the surface is in contact with the ultrasound probe and while the variable compression force is applied on the target object, generate a plurality of frames of B-mode ultrasound data while the variable compression force is applied on the target object based on the ultrasound echo signals, generate a plurality of frames of Doppler-mode ultrasound data based on the Doppler gate while the variable compression force is applied on the target object based on the ultrasound echo signals, determine a period for a cycle of the variable compression force from the ultrasound probe based on the Doppler-mode ultrasound data, select two frames of the B-mode ultrasound data based on the period for the cycle of the variable compressive force, and generate an elastic image of the target object based on the selected frames of the B-mode ultrasound data, wherein the processor comprises:
  a filtering section configured to filter the Doppler-mode ultrasound data;
  a center frequency calculating section configured to calculate a center frequency of the filtered Doppler-mode ultrasound data; and
  a period determining section configured to determine the period based on the center frequency; and
  a display unit configured to display the elastic image.

10. The ultrasound system of claim 9, wherein the filtering section comprises a low pass filter.

11. The ultrasound system of claim 9, the plurality of frames of B-mode ultrasound data are generated sequentially, and
  wherein the processor comprises a frame selecting section configured to select a first frame from the plurality of frames of B-mode ultrasound data, and select a second frame from the frames of B-mode ultrasound data preceding the first frame based on the period.

12. The method of claim 11, wherein the second frame precedes the first frame by a specified number of frames, and
  wherein the frame selecting section is configured to calculate the specified number of frames according to the following equation:

$$F = \frac{T \times F_r}{2}$$

wherein F represents the specified number of frames, T represents the period, and $F_r$ represents a frame rate for the frames of the B-mode ultrasound data.

13. The ultrasound system of claim 9, wherein a pulse repetition frequency for each of the plurality of the frames of the Doppler-mode ultrasound data is less than or equal to 100 Hz.

14. The ultrasound system of claim 9, wherein the processor further comprises a guideline generating section configured to generate a guideline configured to guide movement of the ultrasound probe based on the period, and
  wherein the display unit is further configured to display the guideline as a graph.

15. The ultrasound system of claim 9, wherein the processor further comprises a guide sound generating section configured to generate guide sound configured to guide movement of the ultrasound probe based on the period.

16. The ultrasound system of claim 15, further comprising:
  a speaker configured to output the guide sound.

* * * * *